United States Patent

Claudy et al.

[11] Patent Number: 6,076,961
[45] Date of Patent: Jun. 20, 2000

[54] METHOD AND DEVICE FOR DETERMINING THE LOW-TEMPERATURE STABILITY OF A HYDROCARBON MIXTURE

[75] Inventors: Pierre Claudy, Brignais; Yann Faure, Saint Chamond; Jean-Marie Letoffe, Decines; Catherine Mallet, Lyons; Despina Vassilakis, Moulineaux, all of France

[73] Assignee: Elf Antar France, Courbevoie, France

[21] Appl. No.: 09/147,201
[22] PCT Filed: Feb. 26, 1998
[86] PCT No.: PCT/FR98/00373
§ 371 Date: Mar. 16, 1999
§ 102(e) Date: Mar. 16, 1999
[87] PCT Pub. No.: WO98/38488
PCT Pub. Date: Sep. 3, 1998

[30] Foreign Application Priority Data

Feb. 27, 1997 [FR] France .................... 97 02366

[51] Int. Cl.[7] .............. G01N 25/00; G01N 9/02
[52] U.S. Cl. ............................ 374/45; 73/30
[58] Field of Search ............... 374/14, 45, 141, 374/44, 54, 10–13; 73/30

[56] References Cited

U.S. PATENT DOCUMENTS

| | | |
|---|---|---|
| 3,045,472 | 7/1962 | Paulik et al. .................. 374/14 |
| 3,055,206 | 9/1962 | Watson et al. ................. 374/14 |
| 3,135,107 | 6/1964 | Paulik et al. .................. 374/14 |
| 3,438,248 | 4/1969 | Taylor et al. .................. 374/57 |
| 4,425,810 | 1/1984 | Simon et al. .................. 374/45 |
| 4,489,592 | 12/1984 | Pacanowski et al. ........... 73/30 |
| 4,538,447 | 9/1985 | Pravda ......................... 374/45 |
| 5,400,642 | 3/1995 | Salvador Palacios et al. ... 374/45 |
| 5,813,767 | 9/1998 | Calabro' et al. ............... 374/45 |
| 5,844,151 | 12/1998 | Brown et al. .................. 374/45 |

*Primary Examiner*—G. Bradley Bennett
*Assistant Examiner*—Gail Verbitsky
*Attorney, Agent, or Firm*—Oblon, Spivak, McClelland, Maier & Neustadt, P.C.

[57] ABSTRACT

The invention concerns a method for determining the temperature stability of a hydrocarbon mixture capable of phase separation by monitoring the weight variations of a gravimetric sensor part of which is immersed in said mixture. The method consists in: a first step of accelerated cooling of said mixture to a predetermined temperature; and a second step during which said mixture is maintained at this temperature, the time-dependent variation curve of said weight enabling the determination of the resulting solid mass and the separation speed of the two phases by determining the slope of this curve, the stability of said mixture being obtained by comparison with hydrocarbon mixtures of which the stability in time at low temperature between 0 and −30° C. has been controlled.

9 Claims, 3 Drawing Sheets

GENERAL FORM OF THE SEDIMENTATION CURVES OBTAINED
WITH AN UNDOPED COMMERCIAL GAS OIL

SEDIMENTATION CURVE

METHOD AND DEVICE FOR DETERMINING THE LOW-TEMPERATURE STABILITY OF A HYDROCARBON MIXTURE

The present invention relates to a procedure for determining the low-temperature stability of a hydrocarbon mixture of the gas oil, fuel oil or crude oil type.

This procedure may be used to determine the stability of a gas oil which, on cooling, separates into two phases because of the crystallization followed by sedimentation (or creaming) of solid paraffins or waxes within the hydrocarbon mixture.

This procedure is particularly suitable, in the oil industry, for measuring the sedimentation of waxes in gas oils.

Most crude or refined hydrocarbons contain quite a high proportion of n-alkanes, called paraffins. These paraffins, due to the effect of a drop in temperature, can undergo crystallization and then sedimentation and thus cause malfunctions in the engines (gas oil), heating installations (fuel oil) or pipelines (crude oil) where these hydrocarbons are used.

Thus, the possibility of predicting the conditions under which an apparently homogeneous liquid hydrocarbon might separate into two phases is a considerable advantage for the optimum use of this hydrocarbon.

For example, when the temperature of a gas oil is lowered to between 0° C. and −30° C., the fact of knowing below which temperature the heavy phase crystallizes and of knowing how it does so, the light fraction remaining in the liquid state, makes it possible to fix the conditions of storage and of use of this gas oil so that it remains in the form of a homogeneous liquid phase. Thus, it is possible to prevent pipes and filters from becoming blocked and to avoid the pumping difficulties manifested by unstable operation of diesel engines.

There are several characteristic temperatures of gas oils: the cloud point or temperature at which the first wax crystals appear, the cold filter-plugging point (CFPP) or temperature at which a filter of standardized mesh size becomes blocked, and the pour point or the temperature below which the liquid cannot flow.

Waxes are found in all heavy hydrocarbons, such as domestic fuels, heavy fuels, crude oils and bitumens, and also cause filtering, pumping and blocking problems, especially in industrial and domestic boilers. In the case of domestic fuel oils, it is common to speak of summer fuel oil and winter fuel oil depending on their acceptable wax content during these periods.

In order to prevent the appearance of the phenomenon of crystallization followed by sedimentation, additives, whose function is to delay the appearance of crystals, prevent their development, keep them in suspension or prevent their sedimentation, are added to the hydrocarbons. It is therefore important to measure the impact of these additives on these phenomena.

There are several methods for measuring the parameters which characterize the appearance and separation of a solid phase within the liquid.

One method is based on measuring the weight of solids, such as waxes, in gas oils that have crystallized at a given temperature. These waxes are extracted from the hydrocarbon by centrifuging (Patent EP-0,355,053 A2) or by agglomeration of the waxes in a gravity settler (U.S. Pat. No. 4,357,244). These tests only make it possible to determine the total amount of waxes that have crystallized and are able to settle out. They give a measure of the sedimentation by excess.

A second type of test simulates real-time sedimentation in small containers (NF M 07-085 standard) in which hydrocarbons are stored at low temperature for 24 or 48 hours. The appearance and volume of each phase are then visually assessed by the tester, in particular the position of the interface between the two phases. These tests give an approximately qualitative measurement of the sedimentation.

These methods have drawbacks and inadequacies. They are lengthy, since they generally last 24 hours or 48 hours, and are not reliable since they depend entirely on the subjectivity of the observer. But above all, they do not make it possible to measure the amounts of the separated phases, nor to determine the rate of separation of the phases, nor even to explain and quantify the successive states through which the liquid passes when the temperature changes.

The procedure for determining the stability of a hydrocarbon mixture by thermogravimetric analysis, which is the subject of the invention, solves the problem of quantitatively measuring the separation of the solids from a homogeneous liquid.

The subject of the present invention is a procedure for determining the temperature stability of a hydrocarbon mixture liable to undergo phase separation, characterized in that in a first step, the said mixture, originally at ambient temperature (15° C.), is subjected to accelerated cooling, either by quenching it or by gradually decreasing the temperature at a rate generally of between 10 and 0.05° C./min., until the mixture has reached a predetermined temperature and, using thermogravimetric analysis, the loss of apparent weight (W) of the gravimetric detector is continuously measured, a part of which detector is immersed in the mixture, then in a second step, the mixture is held at this temperature while continuously measuring the increase in apparent weight W of the said gravimetric detector using thermogravimetric analysis and the curve of variation of this weight as a function of time simultaneously recorded, then on the one hand, the mass of solid collected and, on the other hand, the rate of separation of the two phases are determined at any time from this curve of variation of the apparent weight W by determining, from the slope of this curve, mainly the initial rate at its break point corresponding to a substantial and continuous increase in the apparent weight W during the second step, and the stability of the sample of the mixture is deduced by comparing these variations in weight and this rate with those of reference hydrocarbon mixtures, the low-temperature stability of which was monitored over time between 0 and −30° C.

From a practical standpoint, it will be particularly advantageous to determine the stability of the mixture around the crystallization temperature of the paraffins. This is the reason why the temperature at which phase separation becomes visible will be chosen as the predetermined temperature.

The expression "visible separation" should be understood to mean separation detectable to the naked eye or by infrared, as described in Patents FR 2,577,319 and FR 2,681,428.

In practice, in order to measure the stability of the gas oil qualitatively and quantitatively, the predetermined temperature will therefore be chosen to be less than or equal to the crystallization temperature of the paraffins and greater than that of the pour point of the gas oil, i.e. a temperature of between the cloud point temperature, determined by the ISO 3015 standard, and the pour point temperature, determined by the ISO 3016 standard.

The advantages of the procedure forming the subject of the invention are the accuracy, reliability and reproducibility of the results obtained both in the case of measuring the variations in weight of the separated phase and in the case of determining the rate of separation of the phases.

In order to allow quantitative determination of the variations in apparent weight W, and more particularly the weight increase $\Delta W$, of the immersed gravimetric detector due to the deposition of waxes that have undergone sedimentation, all that is required is to take the difference between the measurements of the apparent weight of the detector at the beginning and end of the second step of the measurement. The weight increase $\Delta W$ due to the waxes that have been deposited is obtained, at each instant, by subtracting the relative weight $W_S$ of the cradle measured at the start of the steady-state step from the weight W of the cradle measured at the time t:

$$\Delta W = W - W_S.$$

Thus, at each instant, the total mass $M_P$ of waxes that have separated may be calculated by applying the formula (1):

$$M_P W\, d_P/g[d_P - d_L] \tag{1}$$

in which $M_P$ is the total mass of separated phase at a given time t, $d_L$ is the density of the liquid, $d_P$ is the density of the separated phase, $[d_P - d_L]$ is the absolute value of the difference in densities, W is the apparent weight of the detector at the time t and g is the acceleration due to gravity. In order to apply the formula (1) above, the value of $d_L$ is calculated by dividing the measured weight of the detector by its volume, known from its geometry, and the value of $d_P$ is calculated from the values found in the literature, for example SCHAERER A. A. et al., J.A.C.S 77 2017–18 (1995.)

The homogeneous liquid mixture to be separated is at least one petroleum cut hydrocarbon, distilling between 150° C. and 360° C. at atmospheric pressure, of the group consisting of middle distillates, heavy distillates of the fuel type and crude oils.

The subject of the present invention is also a thermogravimetric device for measurement of the separation of a hydrocarbon mixture into two phases, namely a solid phase and a liquid phase, comprising a thermogravimetric balance provided with a gravimetric detector, the part of which detector that is immersed in a container (2) filled with the said hydrocarbon mixture is a cradle (5), the said container being connected to a cooling circuit, the said device being characterized in that the cradle is free and is preferably coaxial with the cylindrical container, the cross-section of which is such that the ratio of the largest diameter of the cradle to the diameter of the container is between 0.1 and 0.9.

The cradle has a cylindrical shape comprising a bottom and rims, the height of which does not exceed the liquid level in the container. The height of the rims is between 0.5 mm and 30 mm and is generally equal to 5 mm.

The characteristics of the present device will become clearer on examining FIGS. 1A, 1B and 1C and the following description of them.

The device, as shown in FIG. 1A, comprises a thermogravimetric beam balance (1) (of the SETARAM type), a container (2) containing the homogeneous liquid mixture (3) to be studied, a temperature-control apparatus (not shown in the drawing) allowing the container to be cooled or heated, and a computer system (not shown in the drawing) for recording and processing the data.

The beam (4) of the balance (1) carries, suspended from the left arm in the drawing, a cradle (5) immersed in the container (2) containing the mixture. The container (2) has a double jacket (6) and, by virtue of a heating or cooling circuit (not shown in the drawing), it allows the temperature of the mixture to be changed.

The cradle (5) has a cylindrical shape, like the container, and comprises a bottom and rims (7).

A conventional optical and magnetic system (10) associated with the balance allows the variations of the weight of the cradle to be measured and recorded.

The application of the procedure and of the device according to the invention is particularly suitable for assessing the effectiveness of the additives, either for preventing separation into two phases, as with wax in gas oils, or for promoting phase separation, as with water/hydrocarbon emulsions, or else for solubilizing several hydrocarbon phases into a single phase, as when mixing incompatible fuel oils.

The characteristics and advantages of the present invention will become clearer on reading the four non-limiting examples given below of how to use the procedure, these examples referring to FIGS. 2 to 4.

EXAMPLE 1

The first example describes the application of the procedure of the invention to monitoring the crystallization and sedimentation of waxes in gas oils.

The procedure is carried out as follows:

A B60-type thermogravimetric balance, with electromagnetic compensation, sold by SETARAM is used. The cradle is a saucer 20 mm in diameter with rims 5 mm in height. It is placed in a cylinder 30 mm in diameter and 100 mm in height, containing the gas oil to be tested.

The cradle is immersed in the container 33 mm below the surface of the gas oil.

Next, the temperature of the gas oil is lowered at a rate of 0.7° C. per minute to –15° C., at which temperature the formation of crystals is visible, and then the container is held at this temperature for six hours.

The variations in relative weight of the cradle while the temperature is being lowered and during the temperature hold are recorded. A decrease in the relative weight of the cradle is then observed, this being due solely to the variations in the density of the gas oil which increases as the temperature decreases, then an increase in the relative weight due to the waxes which form a deposit in the cradle.

Figure 1A:
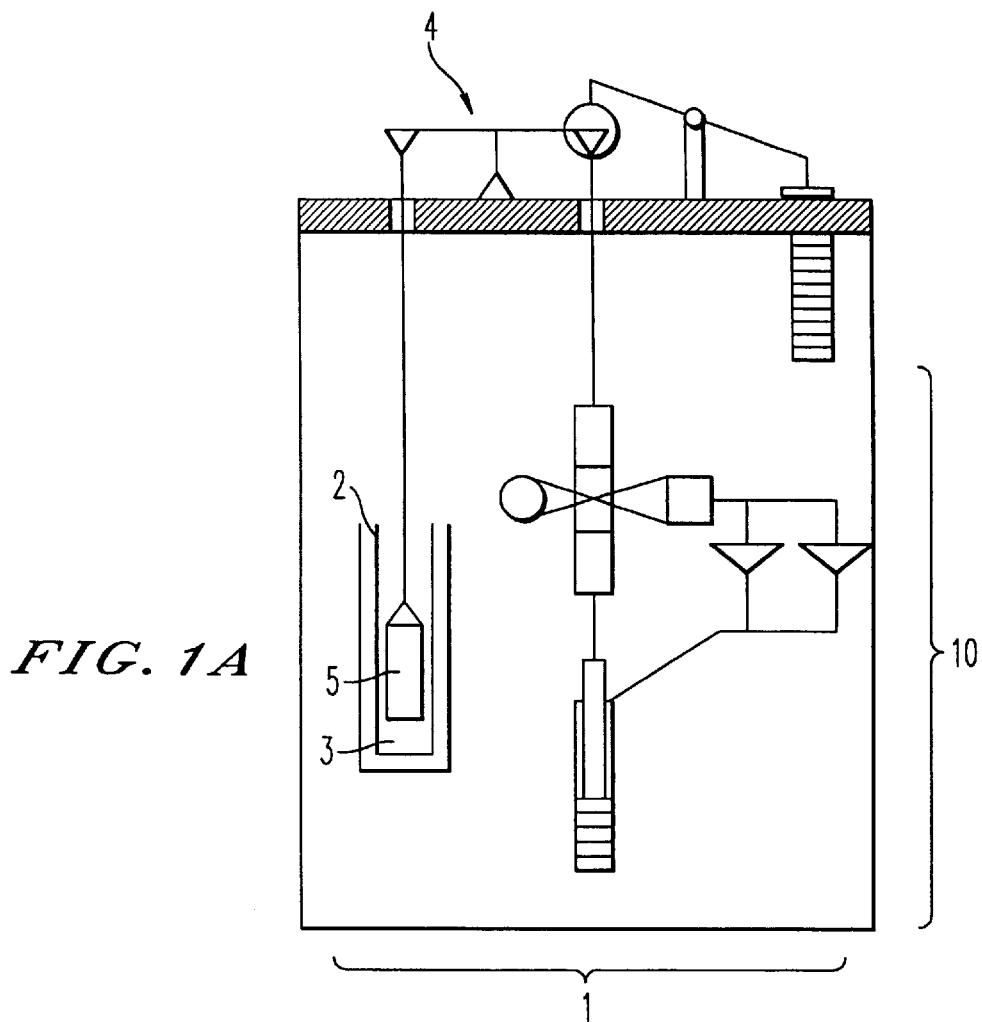
FIGS. 1B and 1C show the details of the cradle.
Figure 1B:
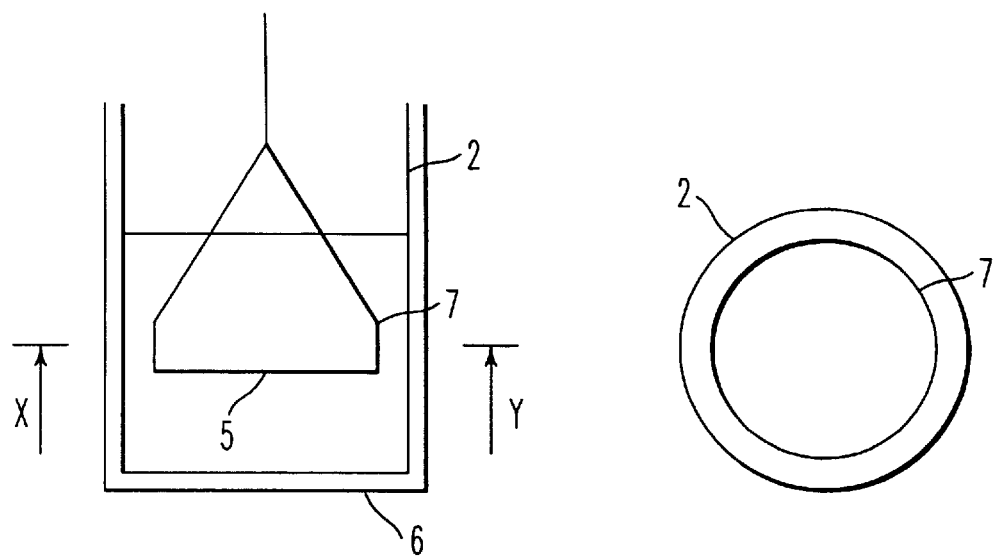
Figure 1C:
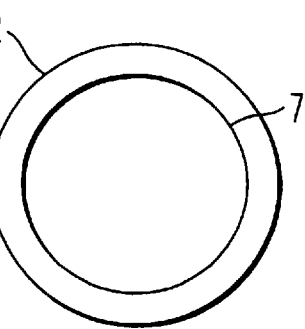
Figure 2A:
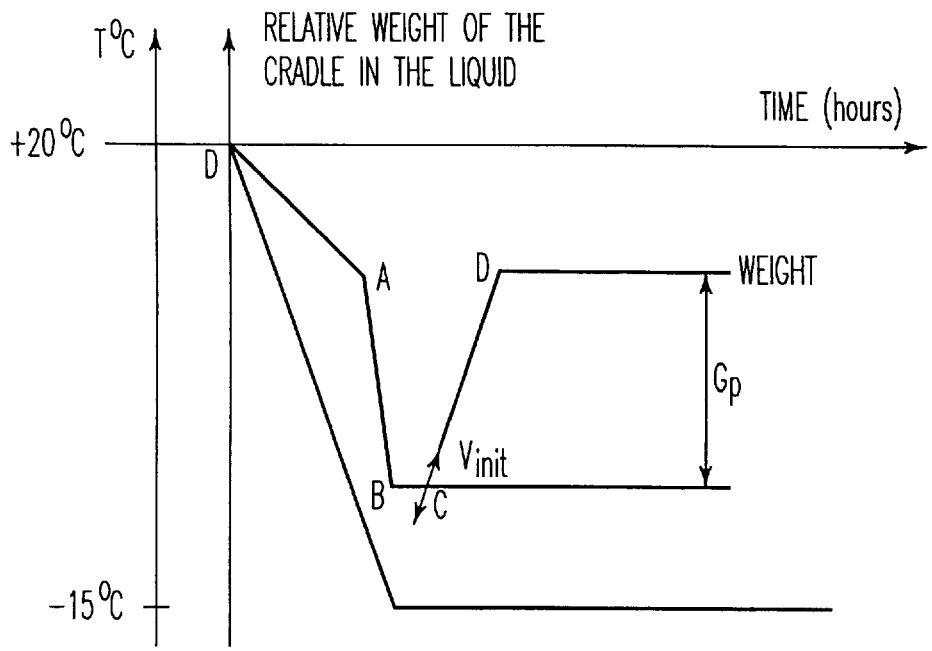
FIGS. 2 and 3 show, in the form of curves, the results of the measurements obtained on various examples of phase separation.

The curve recorded is of the type in the FIG. 2A.

The first part of the curve (OA) is explained by a loss in the apparent relative weight due to the increase in the density of the gas oil as the temperature is being decreased. At point A, the break in slope recorded corresponds to the onset of crystallization of the waxes, or the cloud point. The new slope of the curve (AB) corresponds to a more rapid decrease in the relative weight due to the crystallization of the waxes, the kinetics of which are known to be relatively rapid.

Next, a latent period (part BC) is observed during which the weight does not vary.

The part CD reflects an increase in the relative weight, corresponding to the weight of the waxes which have deposited on the surface of the cradle during the steady-state phase when the temperature is held at, for example, −15° C. (±0.2° C.).

Finally, the present curve has a break D above which the increase in relative weight is zero. At this point, two clearly separate phases are observed. There is then no further sedimentation on the cradle and the measured relative weight remains constant.

The sedimentation curve in FIG. 2A allows two characteristics to be defined:

1/ The increase in relative weight (ΔW) in milligrams, which represents the total amount of wax that has been deposited during the experiment.

2/ The initial rate of sedimentation ($V_{init}$) in mg per hour. The rate of increase of the relative weight is not constant. It is initially rapid, then decreases thereafter. This is because the large particles are deposited quickly, hence a large increase in weight right from the onset of the steady-state phase. Next, the rate of sedimentation decreases, since only the small particles remain, until it becomes zero when all the particles have been deposited. The initial rate of sedimentation therefore allows various gas oils to be compared.

Figure 2B:
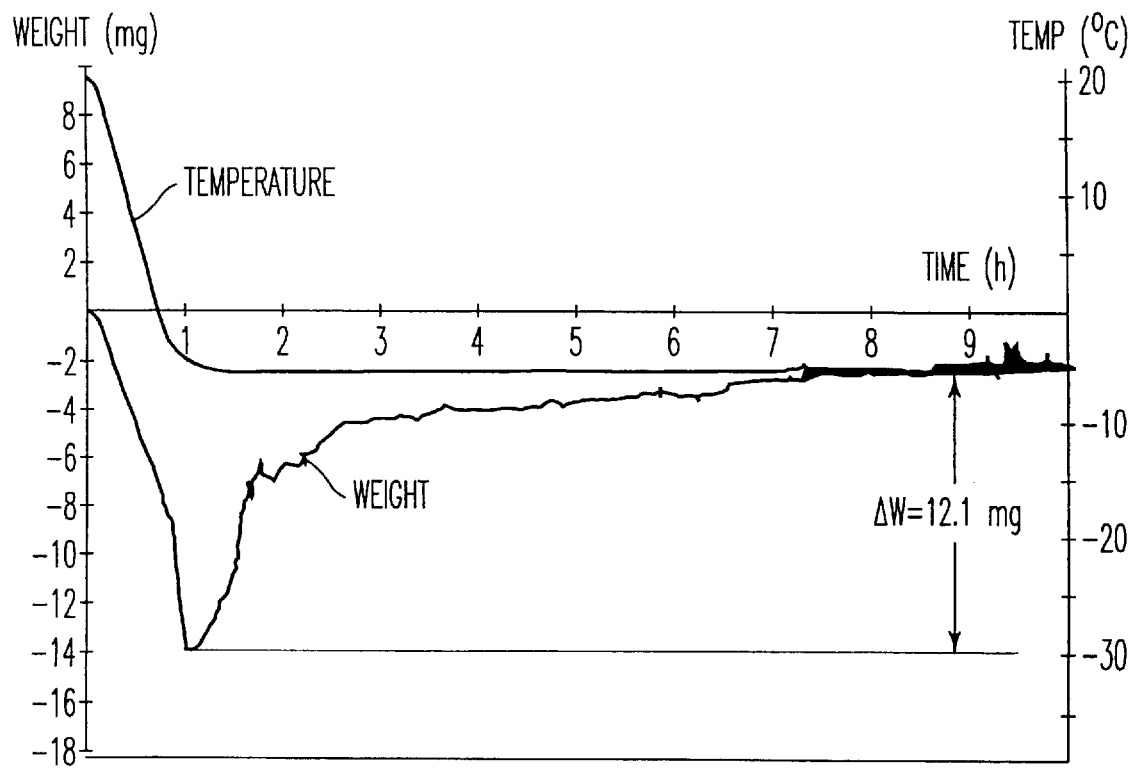

In the case of a gas oil tested and illustrated by the curve in FIG. 2B, it may be seen that the variation in the weight was 12.1 mg.

EXAMPLE 2

The purpose of the second example is to show that the procedure, forming the subject of the invention is quantitative and that the results are in agreement with the theoretical calculations.

The example consists in studying the behaviour of a model gas oil at various hold temperatures during the second step, after proceeding as described in Example 1 for the first step. During each experiment, the increase in relative weight was measured after maintaining these gas oils at these various hold temperatures for 6 hours and these increases were compared with the theoretical weight increases. At each hold temperature there corresponds a theoretical amount of wax that has crystallized, this amount being measured, moreover, by conventional differential calorimetry, as described in the article: FUEL, June 1986, Volume 65, pages 861–864.

A light distillate (kerosene) was chosen as the model gas oil, to which was added a mixture of linear paraffins, the distribution of which is comparable to that encountered in conventional middle distillates, i.e. containing from 6 to 24 carbon atoms. A 4% amount of wax by weight gives a cloud point temperature of −5° C., a cold filter-plugging point of −6° C. and a pour point of −9° C.

Figure 3:
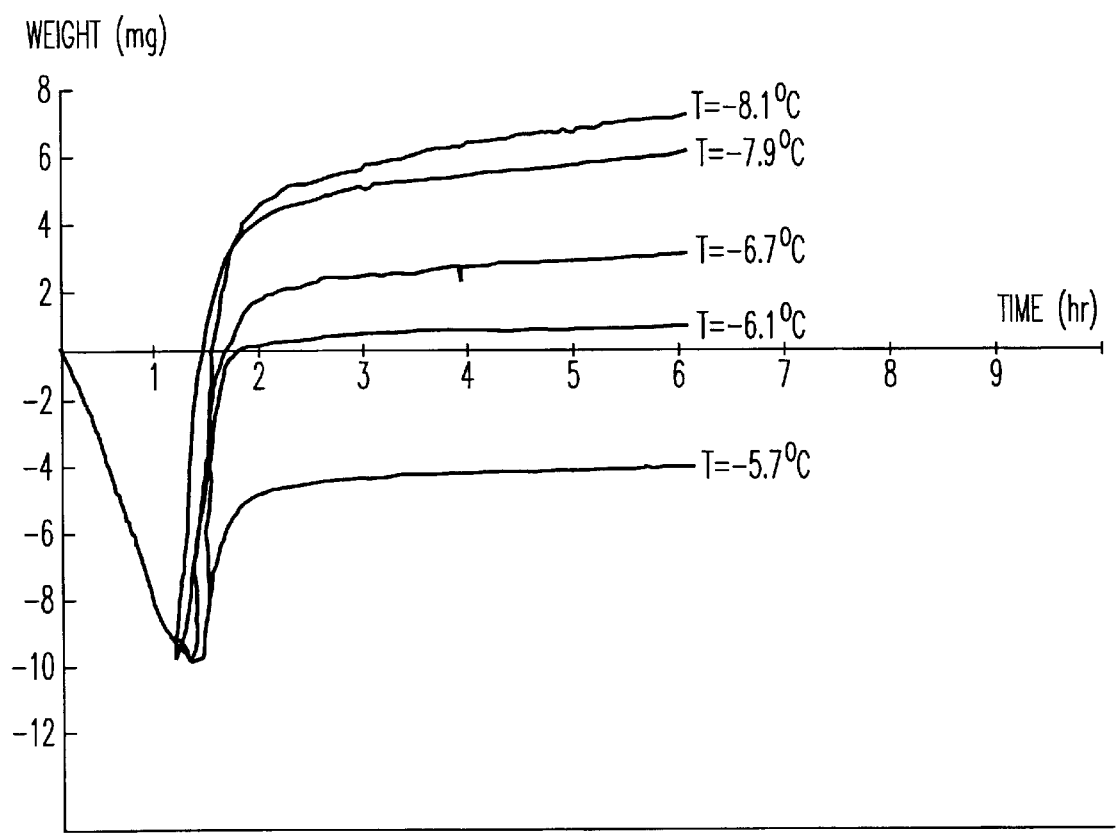

The hold temperature is varied and the effect of this temperature on the amount of wax deposited is observed, as shown by the recorded curves in FIG. 3.

In the absence of an antisedimentation additive, it can be assumed that all the paraffins present in the solid state in the medium are deposited in the weighing cradle during the experiment.

The measured increases in weight of the cradle in the model gas oil as a function of temperature are given in Table 1 below.

TABLE 1

| Temperature (°C.) | −7.3° C. | −6.7° C. | −5.1° C. |
|---|---|---|---|
| Weight increase ΔW measured according to the procedure forming the subject of the invention (mg) | 15.9 | 12.8 | 10.4 |
| Theoretical weight (*) of all the crystallized waxes (mg) | (17.3) | (13.0) | (10.3) |

It may be seen that, for average amounts of crystallized waxes, there is a correlation between the results obtained by the procedure forming the subject of the invention and the results obtained by micro-calorimetry. This procedure therefore is indeed quantitative.

EXAMPLE 3

This example shows the use of the procedure for measuring the effectiveness of the antisedimentation additives.

Comparative sedimentation tests were made between two series of commercial gas oils. The following gas oils were used:

X gas oils containing 250 ppm (250 mg/kg) of KEROF-LUX 3144 filterability additive from BASF so as to obtain a cold filter-plugging point of less than or equal to −15° C. They will be called undoped gas oils;

Y gas oils, identical to the X gas oils, to which 375 ppm of CP 9555 antisedimentation additive from ELF were added. They will be called doped gas oils.

The series of X gas oils consists of six commercial gas oils having different compositions and characteristics. Their respective cloud points, cold filter-plugging points (CFPP) and pour points are given in Table 2 below.

TABLE 2

| Type of gas oil | Cloud point °C. | CFPP °C. | Pour point °C. | % of wax |
|---|---|---|---|---|
| X1 | −1 | −1 | −6 | 7.3 |
| X2 | −7 | −7 | −12 | 15.9 |
| X3 | −5 | −5 | −15 | 15.4 |
| X4 | −6 | −6 | −12 | 12.6 |
| X5 | −4 | −5 | −12 | 13.5 |
| X6 | −6 | −7 | −12 | 14.9 |

Sedimentation tests were carried out according to the procedure described in Example 1.

Table 3 gives the results obtained for the Y doped gas oils and the X undoped gas oils.

TABLE 3

| Undoped gas oil | X1 | X2 | X3 | X4 | X5 | X6 |
|---|---|---|---|---|---|---|
| CFPP (°C.) | −15 | −16 | −17 | −17 | −19 | −19 |
| $V_{init}$ (mg/h) | 11.4 | 6.1 | 2.3 | 6.0 | 6.0 | 5.8 |
| ΔW (mg) | 10.8 | 12.4 | 8.4 | 12.7 | 10.3 | 9.4 |
| Doped gas oil | Y1 | Y2 | Y3 | Y4 | Y5 | Y6 |
| $V_{init}$ (mg/h) | 5.6 | 7.3 | 0.8 | 1.6 | 3.9 | 2.7 |
| ΔW (mg) | 7.1 | 4.5 | 2.8 | 2.0 | 1.7 | 2.1 |
| E* (%) | 34 | 64 | 68 | 84 | 83 | 78 |

*E = effectiveness of the antisedimentation additive.

It may be seen firstly that, for similar weight increases, the initial rate $V_{init}$ can vary from a factor of one to a factor of two depending on the quality of the gas oils, i.e. on the percentage and nature of the waxes that they contain.

Examination of Table 3 shows that there are several major differences, all associated with the action of the antisedimentation additive:

1/ The weight increase ΔW is greatly reduced;

2/ The initial rate of sedimentation for the doped gas oil is markedly less than that obtained for the undoped gas oil, this being a good manifestation of the effect of the antisedimentation additive, whose purpose is to decrease the rate of sedimentation of the crystals;

3/ The curves no longer have as sharp a break at point D. The rate of sedimentation decreases slowly until it becomes zero and two separate phases are no longer observed; and 4/ Comparison between the results obtained with and without the antisedimentation additive allows the effectiveness E of the additive in the gas oil to be calculated by applying the following equation:

$$E=[1-(\Delta W(\text{doped gas oil})/\Delta W(\text{undoped gas oil})]\times 100.$$

What is claimed is:

1. A process for determining temperature stability of a hydrocarbon mixture liable to undergo phase separation, which comprises:
    a) in a first step, subjecting the mixture at ambient temperature, to accelerated cooling, either by quenching or by gradually decreasing the temperature at a rate of between about 10 and 0.05° C./min., until the mixture has reached a predetermined temperature, and, continuously measuring loss of apparent weight (W) of a gravimetric detector b thermogravimetric analysis wherein a portion of the detector is immersed in the mixture, then
    b) in a second step, maintaining the mixture at this temperature while continuously measuring an increase in apparent weight of the detector and simultaneously recording a curve of variation of the weight as a function of time, then
    c) collecting the mass of solid and determining the rate of separation of the two phases from the curve of variation by determining, from the slope of this curve, an initial rate at break point corresponding to a substantial and continuous increase in the apparent weight W during step b), and
    d) determining the stability of the sample of the mixture by comparing the variations in weight and the initial rate with those of reference hydrocarbon mixtures, the low-temperature stability monitored over time between about 0 and −30° C.

2. The process of claim 1, wherein the predetermined temperature is between a temperature at which solid crystals appear and a pour point of the liquid.

3. The process of claim 1. wherein for liquid/solid separation, a threshold temperature of step b) is less than or equal to the temperature at which solid crystals appear and greater than that of the pour point of the liquid.

4. The process of claim 1, wherein the homogeneous liquid mixture to be separated is at least one petroleum cut hydrocarbon, distilling between about 150° C. and 360° C. at atmospheric pressure, of the group consisting of middle distillates, fuel-type heavy distillates and crude oils.

5. A method of measuring effectiveness of one or more additives to maintain homogeneity of a mixture, which comprises the process of claim 1.

6. A method of measuring solubilization of a plurality of phases into a single phase, which comprises the process of claim 1.

7. A device for continuous quantitative measurement, by thermogravimetric analysis, of a separation of a liquid hydrocarbon mixture into a solid phase and a liquid phase, comprising a thermogravimetric balance provided with a gravimetric detector, a part of which detector is immersed in a container and is filled with the hydrocarbon mixture and is a cradle, wherein the container is connected to a heating or cooling circuit, wherein the cradle is free, the cross-section of which being such that the ratio of the largest diameter of the cradle to the diameter of the container is between about 0.1 and 0.9.

8. The device of claim 7, wherein the cradle has a cylindrical shape comprising a bottom and rims, the height of which is between about 5 mm and 30 mm and is equal to about 5 mm.

9. The device of claim 7, wherein said cradle is coaxial with said container, which container is cylindrical.

* * * * *

UNITED STATES PATENT AND TRADEMARK OFFICE
CERTIFICATE OF CORRECTION

PATENT NO. : 6,076,961

DATED : June 20, 2000

INVENTOR(S): Pierre CLAUDY, et al.

It is certified that an error appears in the above-identified patent and that said Letters Patent is hereby corrected as shown below:

Title page, [75] Inventors, "Catherine Mallet, Lyons;"
should read --Catherine Mallet, Lyon;--.

Column 6, Line 11, insert paragraph --(*) Measurement by conventional microcalorimetry according to the operating method described in the article: FUEL, June 1986, Volume 65, pages 861-864.--.

Signed and Sealed this

Twenty-second Day of May, 2001

Attest:

NICHOLAS P. GODICI

*Attesting Officer*   *Acting Director of the United States Patent and Trademark Office*